(12) United States Patent
Sato et al.

(10) Patent No.: US 8,748,836 B2
(45) Date of Patent: Jun. 10, 2014

(54) PORTABLE RADIOGRAPHIC IMAGING DEVICE AND RADIOGRAPHIC IMAGING SYSTEM

(75) Inventors: Keiichiro Sato, Kanagawa (JP); Yusuke Kitagawa, Kanagawa (JP); Naoto Iwakiri, Kanagawa (JP); Yasunori Ohta, Kanagawa (JP); Haruyasu Nakatsugawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 153 days.

(21) Appl. No.: 13/600,027

(22) Filed: Aug. 30, 2012

(65) Prior Publication Data

US 2013/0075609 A1    Mar. 28, 2013

(30) Foreign Application Priority Data

Sep. 28, 2011  (JP) ................................. 2011-213207

(51) Int. Cl.
*G01T 1/24* (2006.01)
*A61B 6/00* (2006.01)

(52) U.S. Cl.
CPC .. *A61B 6/44* (2013.01); *G01T 1/244* (2013.01)
USPC ..................................... 250/370.09; 378/189

(58) Field of Classification Search
CPC ........ A61B 6/4283; A61B 6/563; A61B 6/44; G01T 1/244
USPC ........................ 250/366, 336.1, 370.1, 370.09
See application file for complete search history.

(56) References Cited

U.S. PATENT DOCUMENTS

| | | | |
|---|---|---|---|
| 7,429,131 B2* | 9/2008 | Watanabe | 378/205 |
| 2002/0011572 A1* | 1/2002 | Kajiwara et al. | 250/370.11 |
| 2002/0014594 A1* | 2/2002 | Endo | 250/370.09 |
| 2005/0184244 A1* | 8/2005 | Yoshimuta et al. | 250/370.01 |

FOREIGN PATENT DOCUMENTS

JP          2002-158341 A      5/2002

* cited by examiner

*Primary Examiner* — David Porta
*Assistant Examiner* — Yara B Green
(74) *Attorney, Agent, or Firm* — Jean C. Edwards; Edwards Neils PLLC

(57) ABSTRACT

A portable radiographic imaging device including: a radiation detection panel including optoelectric conversion elements that convert irradiated radiation into an electrical signal; a signal processing substrate performing predetermined signal processing on the input electrical signal; a holding base provided between the radiation detection panel and the signal processing substrate and holding the signal processing substrate; a flexible substrate including a flexed portion, with one end of the flexible substrate being connected to the radiation detection panel and the other end of the flexible substrate being connected to the signal processing substrate; a casing in which the radiation detection panel, the signal processing substrate, the holding base and the flexible substrate are installed; and a contact avoidance portion formed at at least one of the signal processing substrate, the holding base or the casing such that contact of with the flexible substrate is avoided, is provided.

16 Claims, 10 Drawing Sheets

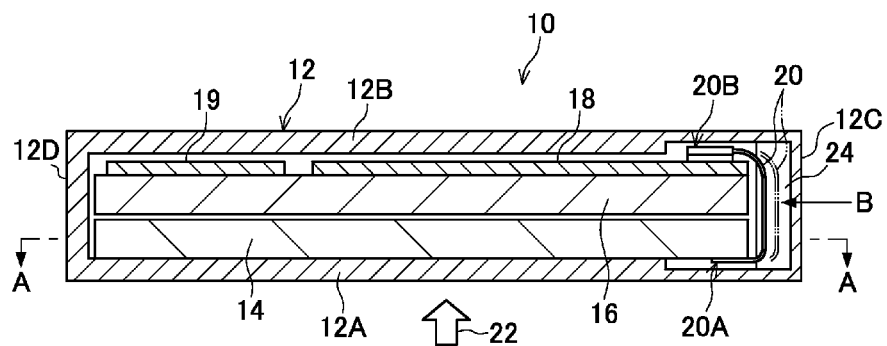
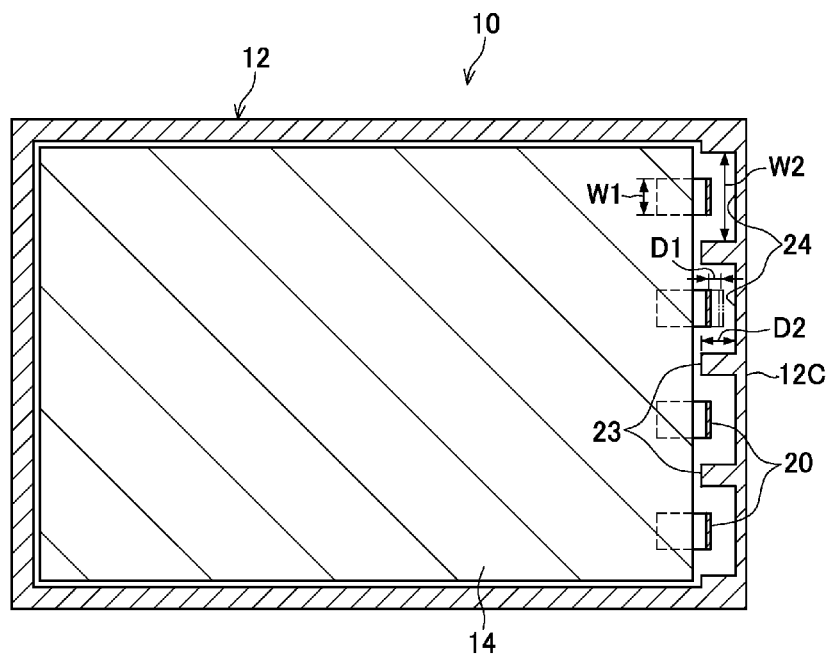

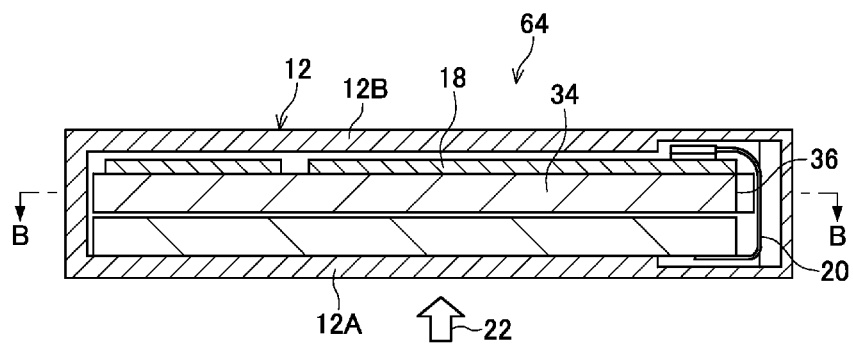
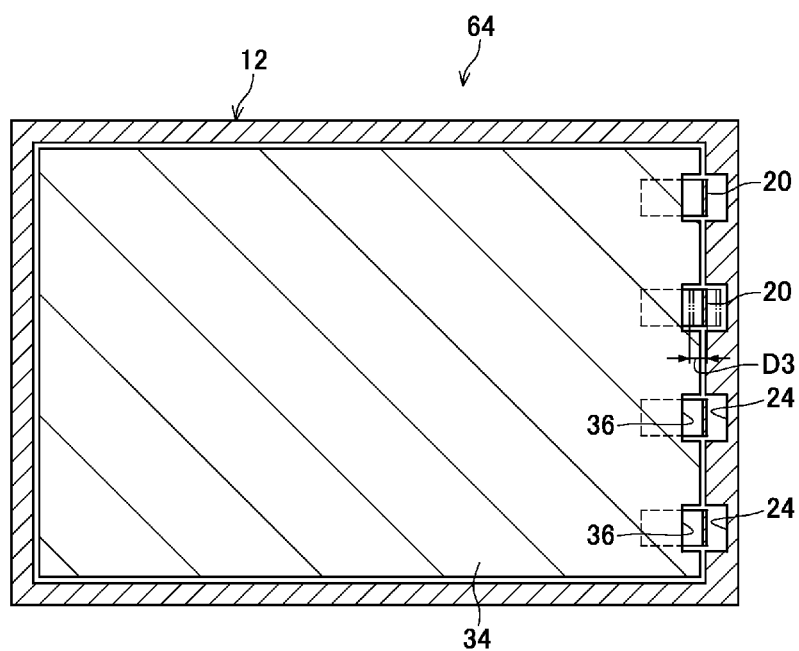

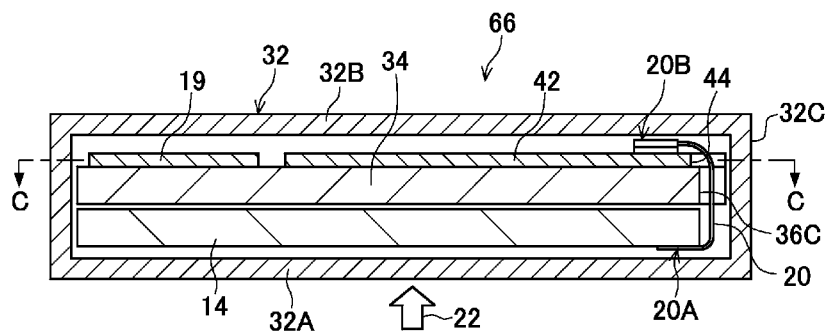
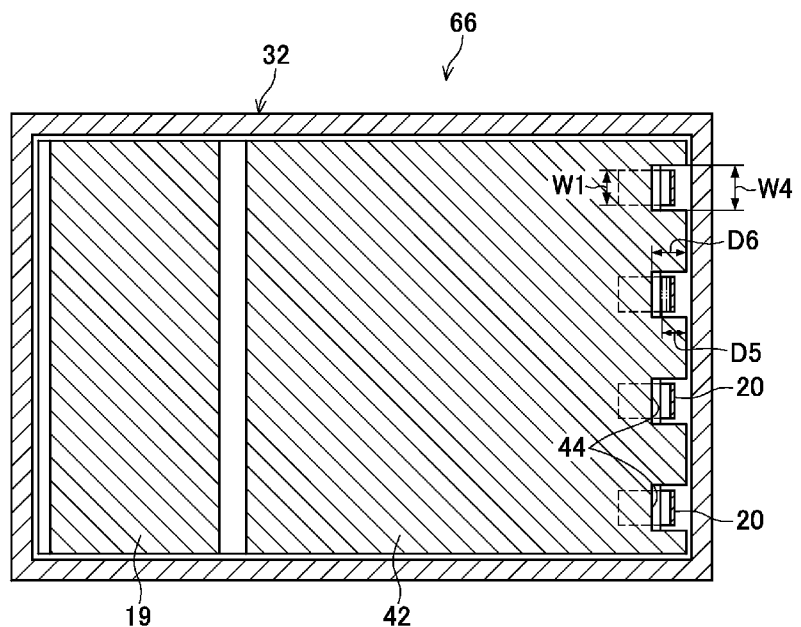

PORTABLE RADIOGRAPHIC IMAGING DEVICE AND RADIOGRAPHIC IMAGING SYSTEM

CROSS-REFERENCE TO RELATED APPLICATION

This application claims priority under 35 USC 119 from Japanese Patent Application No. 2011-213207 filed Sep. 28, 2011, the disclosure of which is incorporated by reference herein.

BACKGROUND

1. Field of the Invention

The present invention relates to a portable radiographic imaging device in which a radiation detection panel and a signal processing substrate are connected by a flexible substrate, and a radiographic imaging system including a portable radiographic imaging device.

2. Description of the Related Art

A radiation detector is recently being implemented that uses a Flat Panel Detector (FPD) in which a radiation sensitive layer is disposed on a Thin Film Transistor (TFT) active matrix substrate, and which is capable of converting radiation directly into digital data. Accompanying this, a portable radiographic imaging device (referred to hereafter as an electronic cassette) that uses the FPD and is designed for thinness and lightness for carrying around is also becoming widespread.

An issue accompanying thinner electronic cassettes is that, since space between components is reduced, when the electronic cassette is imparted with a vibration, a flexible substrate may deform and contact with components near the flexible substrate. In a case in which such a flexible substrate contacts with the components near the flexible substrate, noise is generated and there is deterioration in image quality with the electronic cassette. Technology is proposed (in Japanese Patent Application Laid-Open (JP-A) No. 2002-158341: Patent Document 1) that reduces the influence of vibration even in thinner model in order to address this issue.

An X-ray imaging device disclosed in Patent Document 1 is configured with a printed circuit substrate that converts an irradiated X-ray into an electrical signal, and a signal processing substrate that processes input electrical signal, disposed facing each other with a base stand supporting the signal processing substrate interposed therebetween. The printed circuit substrate is connected to the signal processing substrate by a flexible circuit substrate, and a central portion of the flexible circuit substrate is fixed with a screw to an end portion of the base stand.

Such a configuration restricts deformation of the flexible circuit substrate even when a vibration is imparted to the X-ray imaging device, thereby restricting contact between the flexible circuit substrate and components near the flexible circuit substrate.

However, in JP-A No. 2002-158341, the technique used to restrict movement of the flexible circuit substrate is that the both end portions of the flexible circuit substrate are respectively connected to the printed circuit substrate and the signal processing substrate, and the central portion of the flexible circuit substrate is fixed with the screw to the end portion of the base stand.

Accordingly, when the X-ray imaging device is imparted with a vibration, causing relative movement between the printed circuit substrate and the signal processing substrate, tension may act through the flexible circuit substrate on the connection portion between the flexible circuit substrate and the printed circuit substrate and/or on the connection portion between the flexible circuit substrate and the signal processing substrate. If such tension is high, this causes poor connection in the connection portions and an accompanying generation of noise. Namely, a technique to restrict deformation of the flexible circuit substrate by fixing the central portion of the flexible circuit substrate with the screw gives rise to new issues, rendering such a method undesirable.

SUMMARY

In consideration of the above circumstances, the present invention provides a portable radiographic imaging device in which a flexible substrate does not contact with components peripheral thereto, without restricting deformation of the flexible circuit substrate.

A portable radiographic imaging device of a first aspect of the present invention includes: a radiation detection panel that includes optoelectric conversion elements that convert irradiated radiation into an electrical signal; a signal processing substrate that performs predetermined signal processing on the input electrical signal; a holding base that is provided between the radiation detection panel and the signal processing substrate and that holds the signal processing substrate; a flexible substrate that includes a flexed portion, with one end of the flexible substrate being connected to the radiation detection panel and the other end of the flexible substrate being connected to the signal processing substrate; a casing in which the radiation detection panel, the signal processing substrate, the holding base and the flexible substrate are installed; and a contact avoidance portion that is formed at at least one of the signal processing substrate, the holding base or the casing such that contact of the at least one of the signal processing substrate, the holding base or the casing with the flexible substrate is avoided.

According to the first aspect of the present invention, radiation is converted into electrical signals by the radiation detection panel provided with optoelectric conversion elements, and predetermined signal processing is performed by the signal processing substrate on the input electrical signals. The signal processing substrate is held by the holding base provided between the radiation detection panel and the signal processing substrate, and the radiation detection panel and the signal processing substrate are connected by the flexible substrate provided with a flexed portion. Contact is avoided between the flexible substrate and the signal processing substrate, the holding base and the casing due to forming the contact avoidance portion on at least one of the signal processing substrate, the holding base and/or the casing.

As a result, relative displacement is absorbed by the flexed portion provided at the flexible substrate even if the portable radiographic imaging device is imparted with a vibration and relative displacement occurs between the radiation detection panel and the signal processing substrate. Tension accordingly does not act on a connection portion between the flexible substrate and the radiation detection panel and/or on a connection portion between the flexible substrate and the signal processing substrate, and poor contact can be prevented at the connection portions at both ends of the flexible substrate.

A portion of the flexible substrate other than the connection portions are restricted from making contact with peripheral components due to the contact avoidance portion, and so noise generated from contact with the peripheral component can be suppressed. Namely, the portable radiographic imaging device can be provided in which the flexible substrate does not make contact with the peripheral components thereto even without restricting deformation of the flexible substrate.

As a modified aspect of the first aspect, the portable radiographic imaging device of the first aspect further includes an amplify section that amplifies the input electrical signal, provided at the flexible substrate.

A second aspect of the present invention is the portable radiographic imaging device of the first aspect in which the contact avoidance portion is a casing concave portion that is provided at an inner wall of the casing at a position facing the flexible substrate, and a width of the casing concave portion is wider than a width of the flexible substrate.

According to the second aspect of the invention, the casing concave portion is formed in the inner wall of the casing, facing the flexible substrate and with a width that is wider than the width of the flexible substrate.

The flexible substrate can accordingly be prevented from making contact with the casing even if the portable radiographic imaging device is imparted with a vibration.

A third aspect of the present invention is the portable radiographic imaging device of the first or the second aspect in which the contact avoidance portion is a base concave portion that is provided at an end portion of the holding base at a position facing the flexible substrate, and a width of the base concave portion is wider than the width of the flexible substrate.

According to the third aspect of the present invention, the base concave portion is formed at the end face of the holding base, facing the flexible substrate and with a width wider than the width of the flexible substrate.

The flexible substrate and the end face of the holding base can accordingly be prevented from making contact with each other even if the portable radiographic imaging device is imparted with a vibration.

A fourth aspect of the present invention is the portable radiographic imaging device of any one of the first to the third aspects in which the contact avoidance portion is a substrate concave portion that is provided at an end portion of the signal processing substrate at a position facing the flexible substrate, and a width of the substrate concave portion is wider than the width of the flexible substrate.

According to the fourth aspect of the present invention, the substrate concave portion is formed at the end face of the signal processing substrate, facing the flexible substrate and formed with a width wider than the width of the flexible substrate.

The flexible substrate and the end face of the signal processing substrate can accordingly be prevented from making contact with each other even if the portable radiographic imaging device is imparted with a vibration.

A fifth aspect of the present invention is the portable radiographic imaging device of any one of the first to the third aspects in which the contact avoidance portion is a chamfered portion that is provided at an end face of the signal processing substrate at a position facing the flexible substrate, and a width of the chamfered portion is wider than the width of the flexible substrate.

According to the fifth aspect of the present invention, the chamfered portion is provided to the end face of the signal processing substrate, facing the flexible substrate and with a width wider than the width of the flexible substrate.

The flexible substrate and the end face of the signal processing substrate can accordingly be prevented from making contact even if the portable radiographic imaging device is imparted with a vibration.

A sixth aspect of the present invention is the portable radiographic imaging device of the second aspect further including a rib portion that maintains strength of the casing, the rib portion being formed between adjacent casing concave portions.

The strength of the casing can accordingly be maintained even if the casing concave portion is provided at the casing.

A seventh aspect of the present invention is the portable radiographic imaging device of any one of the first to the sixth aspects in which the flexed portion of the flexible substrate is a bent portion that is bent to be away from end portions of the radiation detection panel, the signal processing substrate and the holding base.

Relative displacement between the radiation detection panel and the signal processing substrate when vibration occurs in the portable radiographic imaging device can accordingly be absorbed by the flexed portion configured by the bend portion of the flexible substrate.

An eighth aspect of the present invention is the portable radiographic imaging device of any one of the first to the sixth aspects in which the flexed portion of the flexible substrate is a folded portion including a plurality of foldings in the flexible substrate.

Relative displacement between the radiation detection panel and the signal processing substrate when vibration occurs in the portable radiographic imaging device can accordingly be absorbed by the flexed portion configured by the folded portion of the flexible substrate.

A ninth aspect of the present invention is the portable radiographic imaging device of any one of the third to the fifth aspects, the seventh or the eighth aspects in which a depth of the casing concave portion in a case in which the base concave portion is formed at the holding base facing the casing concave portion is set shallower than a depth of the casing concave portion in a case in which the base concave portion is not formed at the holding base facing the casing concave portion.

Any reduction in strength of the casing due to provision of the casing concave portion can accordingly be suppressed.

A tenth aspect of the present invention is the portable radiographic imaging device of any one of the fourth, fifth or seventh to ninth aspects in which a depth of the casing concave portion in a case in which the substrate concave portion is formed at the signal processing substrate facing the casing concave portion is set shallower than a depth of the casing concave portion in a case in which the substrate concave portion is not formed at the signal processing substrate facing the casing concave portion.

Any reduction in strength of the casing due to provision of the casing concave portion can accordingly be suppressed.

A radiographic imaging system according to an eleventh aspect of the present invention includes: the portable radiographic imaging device of any one of the first to the tenth aspects; a radiation generating device that generates radiation; and an imaging controller that controls the portable radiographic imaging device and the radiation generating device, in which, under control of the imaging controller, radiation is generated by the radiation generating device and the portable radiographic imaging device images the radiation that passes through a subject.

Radiographic imaging can accordingly be performed by the radiographic imaging system including the portable radiographic imaging device.

Due to the above configuration, the present invention can provide a portable radiographic imaging device in which a flexible circuit substrate does not make contact with components peripheral thereto, without restricting deformation of the flexible circuit substrate.

BRIEF DESCRIPTION OF THE DRAWINGS

Exemplary embodiments of the present invention will be described in detail based on the following figures, wherein:

FIG. 1A is a vertical cross-section illustrating a basic configuration of a portable radiographic imaging device according to a first exemplary embodiment of the present invention, and FIG. 1B is a cross-section taken along line A-A of FIG. 1A;

FIG. 7A is a vertical cross-section illustrating a basic configuration of a portable radiographic imaging device according to a sixth exemplary embodiment of the present invention, and FIG. 7B is a cross-section taken along line A-A of FIG. 7A;

FIG. 9A is a vertical cross-section illustrating a basic configuration of a portable radiographic imaging device according to an eighth exemplary embodiment of the present invention, and FIG. 9B is a cross-section taken along line C-C of FIG. 9A;

DETAILED DESCRIPTION

First Exemplary Embodiment

Figure 2:
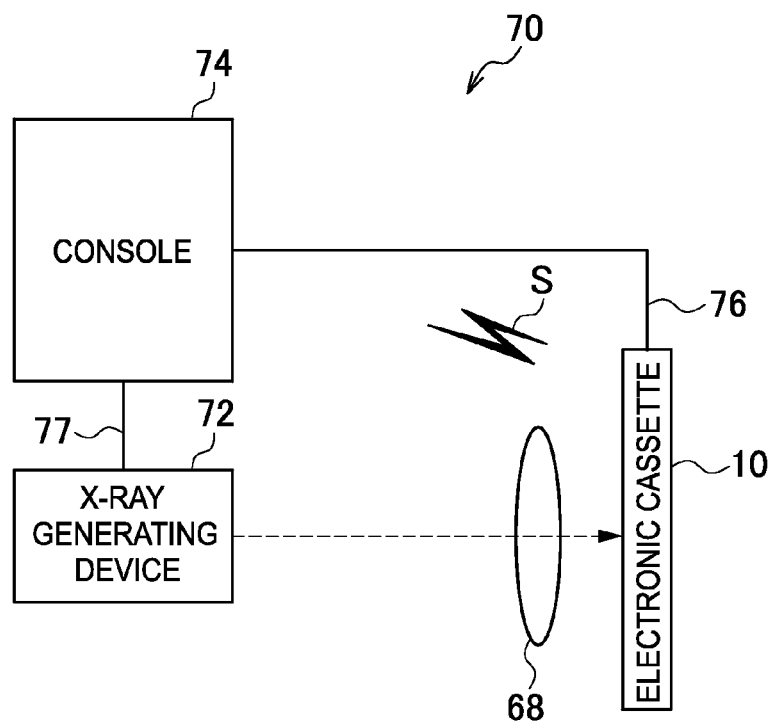
FIG. 2 is a schematic diagram illustrating a basic configuration of a radiographic imaging system employing a portable radiographic imaging device according to the first exemplary embodiment of the present invention.

As shown in the cross-sections of FIG. 1A and FIG. 1B, an electronic cassette 10 according to a first exemplary embodiment has a hollow flat plate shaped casing 12, with various components for X-ray imaging housed in the casing 12. The casing 12 has a rectangular cross-sectional profile with flat panels 12A and 12B, and 12C and 12D mutually facing each other. X-ray is irradiated from the arrow 22 direction when the electronic cassette 10 is in use.

The casing 12 is formed for example from a resin or metal material, with dimension and shape that render the casing 12 portable.

A flat panel sensor section 14 is provided inside the casing 12. The flat panel sensor section 14 is disposed to surface-face the flat panel 12A on the X-ray irradiated side, and has a size that covers substantially the entire area of the flat panel 12A. The flat panel sensor section 14 is fixed to the flat panel 12A with fastenings, not shown in the drawings. The flat panel sensor section 14 includes optoelectric conversion elements, not shown in the drawings, converting radiation into electrical signal, and converts radiation that has been irradiated through a subject into electrical signal and outputs the electrical signal.

An electronic substrate 18 is provided inside the casing 12 surface-facing the flat panel 12B that faces to the flat panel 12A. The longitudinal direction of the electronic substrate 18 is arranged parallel to the longitudinal direction of the flat panel sensor section 14.

The electronic substrate 18 is provided with a processing circuit that performs predetermined signal processing on electrical signals input from the flat panel sensor section 14.

A flat panel shaped chassis 16 is further provided inside the casing 12, between the flat panel sensor section 14 and the electronic substrate 18. The chassis 16 is fixed to the casing 12, and the electronic substrate 18 is attached to a face of the chassis 16 at the flat panel 12B side. The chassis 16 is formed over a greater surface area than the electronic substrate 18, and an electronic substrate 19 which is different from the electronic substrate 18 is also attached to the face of the chassis 16 at the flat panel 12B side.

Flexible substrates 20 are provided at the inner side of the side wall 12C of the electronic cassette 10. The flexible substrate 20 is a strip shaped conducting cable (with width W1). One end of the flexible substrate 20 is connected to the flat panel sensor section 14 with a connection portion 20A, and the other end of the flexible substrate 20 is connected to the electronic substrate 18 with a connection portion 20B.

The flat panel sensor section 14 and the electronic substrate 18 are thereby electrically connected to each other, and electrical signals converted from irradiated X-rays are transmitted from the flat panel sensor section 14 to the electronic substrate 18. The flexible substrate 20 in the present exemplary embodiment is not fixed at any peripheral location of the flexible substrate 20 other than at the connection portions 20A and 20B.

At the connection portion 20A, joining is done by thermo-compression bonding in which abut faces are joined together by pressing in heated state. At the connection portion 20B, a connector connection is applied in which a connector provided to the flexible substrate 20 is pushed into a terminal base provided to the electronic substrate 18.

Note that these methods of connection of the connection portion 20A and connection portions 20B are merely examples thereof and there is no limitation thereto. At the connection portion 20B, the thermo-compression bonding may be applied, and at the connection portion 20A, the connector connection may be applied. Furthermore, at the connection portion 20A and the connection portion 20B, the thermo-compression bonding may be applied, and at the connection portion 20A and the connection portion 20B, the connector connection may be applied.

A bend (bent) portion (flexed portion) is provided to the flexible substrate 20 at a location other than at the connection portion 20A and the connection portion 20B. The bend portion is across over (straddled), but is not to make contact with (so as to be away from), the respective end portions of the electronic substrate 18, the chassis 16 and the flat panel sensor section 14.

Thus even if relative displacement of the flat panel sensor section 14 and the electronic substrate 18 occurs, the bend portion is able to absorb (accommodate) such relative displacement. As a result tension can be suppressed from acting on the connection portion 20A and the connection portion 20B.

Cutaway portions (casing concave portions) 24 serving as contact avoidance portions are provided on the inner wall of the casing 12 so as to avoid contact with the flexible substrates 20. The casing concave portion 24 is formed such that, on the inner wall of the casing 12 at a position facing to the flexible substrate 20, a width W2 of the casing concave portion 24 is wider than the width W1 of the flexible substrate 20. Ribs 23 are formed between adjacent casing concave portions 24. Reduction in the strength of the casing 12 is suppressed by provision of the ribs 23.

The casing concave portion 24 is formed with a depth D2 that exceeds a deformable range of the bend portion of the flexible substrate 20 towards the side wall 12C such that even if the electronic cassette 10 is imparted with a vibration and the bend portion of the flexible substrate 20 deforms towards the side wall 12C, contact of the side wall 12C and the flexible substrate 20 is avoided.

Due to such a configuration, relative displacement is absorbed by the flexed portion provided to the flexible substrate 20 even if the electronic cassette 10 is imparted with a vibration and the flat panel sensor section 14 and the electronic substrate 18 are relatively displaced. Tension on the connection portions 20A and 20B is thereby suppressed from occurring.

Contact between the flexible substrate 20 and the casing 12 can also be prevented even if the flexible substrate 20 deforms by a maximum dimension D1 towards the inner wall of the casing 12, due to provision of the casing concave portion 24.

Explanation follows regarding operation of the electronic cassette 10 of the present exemplary embodiment. In a case in which X-rays are irradiated in the arrow 22 direction onto the electronic cassette 10, irradiated X-rays are converted into electrical signals by the flat panel sensor section 14 provided with optoelectric conversion elements. The converted electrical signals are transmitted through the flexible substrate 20 to the electronic substrate 18 provided facing to the flat panel sensor section 14. Predetermined signal processing is then performed by the electronic substrate 18 on the electrical signals that have been transmitted to the electronic substrate 18.

Explanation follows regarding the advantageous effects of the present exemplary embodiment.

According to the present exemplary embodiment, tension does not act on the both end portions of the flexible substrate 20 even if the electronic cassette 10 is imparted with a vibration, and so poor connection at the connection portion (the thermo-compression bonding portion) 20A and the connection portion (the connector connection portion) 20B can be suppressed from occurring, and noise that accompanied poor connection can also be suppressed.

Contact of the casing 20 with the flexible substrate 20 at portions other than the connection portions 20A and 20B is also restricted due to provision of the casing concave portions 24, and so noise due to contact between the flexible substrate 20 and peripheral components (components near the flexible substrate 20) can be suppressed from occurring.

Namely, the electronic cassette 10 can be provided in which the flexible substrate 20 does not make contact with the casing 12 even without restricting deformation of the flexible substrate 20.

Explanation follows regarding use-example of the electronic cassette 10 of the present exemplary embodiment.

As shown in the system outline diagram of FIG. 2, the electronic cassette 10 is incorporated in a radiographic imaging system 70 and used.

The electronic cassette 10 is disposed facing to an X-ray generating (emitting) device 72 that generates X-rays for examination. During operation an imaged subject 68 is disposed between the electronic cassette 10 and the X-ray generating device 72. The electronic cassette 10 and the X-ray generating device 72 are respectively controlled by a console 74.

The electronic cassette 10 and the console 74 are connected by a communication cable 76 or by a wireless signal S, such that information can be received and transmitted therebetween. A communication cable 77 is connected between the X-ray generating device 72 and the console 74, such that information can be received and transmitted therebetween. Normal commercially available equipment may be used for the X-ray generating device 72 and the console 74, and so further explanation thereof is omitted.

This system configuration enables control instructions to be received from the console 74, X-rays to be irradiated by the X-ray generating device 72, and X-rays that have passed through the imaging subject 68 to be imaged (captured as image) by the electronic cassette 10.

Note that X-ray for examination is merely given as an example, and various types of radiation other than X-ray may be used, such as alpha-ray, beta-ray, gamma-ray or neutron-ray.

Second Exemplary Embodiment

Figure 3A:
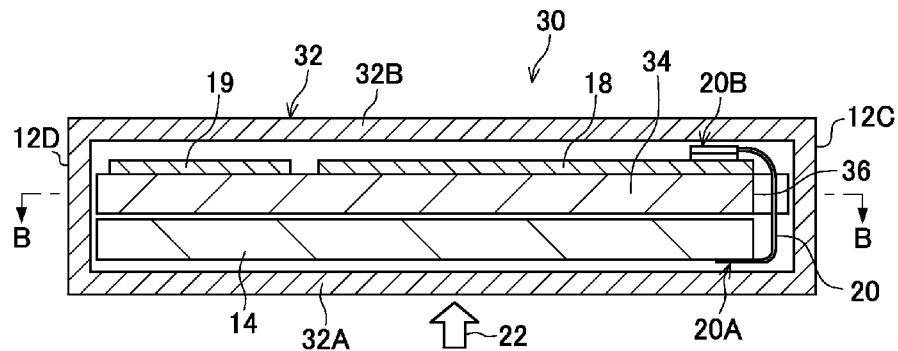
FIG. 3A is a vertical cross-section illustrating a basic configuration of a portable radiographic imaging device according to a second exemplary embodiment of the present invention.
Figure 3B:
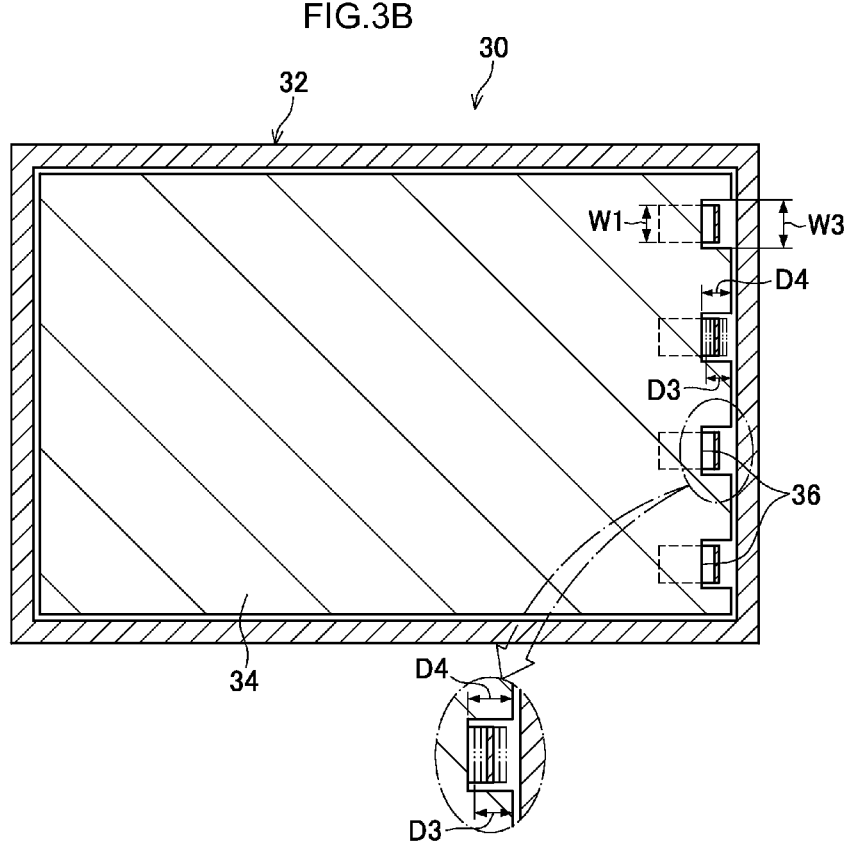
FIG. 3B is a cross-section taken along line B-B of FIG. 3A.

As shown in the cross-sections of FIG. 3A and FIG. 3B, an electronic cassette 30 according to the second exemplary embodiment differs from the first exemplary embodiment by way of the contact avoidance portion provided at the periphery of the flexible substrate 20. Explanation follows focusing on the differences to the first exemplary embodiment.

In the present exemplary embodiment an end portion of a chassis 34 installed in the casing 12 is formed so as to approach the vicinity of the inner wall of the casing 12, so, unless countermeasures are adopted, the flexible substrate 20 would make contact with the end face of the end portion of the chassis 34 when the bend portion of the flexible substrate 20 deforms.

Contact avoidance portions (base concave portions) 36 are accordingly provided at the end portion of the chassis 34 to avoid such contact.

The base concave portion 36 is a cutaway portion provided to the end portion of the chassis 34 at a position facing to the flexible substrate 20, and having a width W3 that is wider than the width W1 of the flexible substrate 20. A depth D4 of the base concave portion 36 is set at a depth such that the flexible substrate 20 does not make contact with the chassis 34 even if the electronic cassette 30 is imparted with a vibration and the flexible substrate 20 deforms towards an end portion (in the depth direction) of the base concave portion 36 by a maximum dimension D3 (D4>D3).

Due to this configuration, contact between the flexible substrate 20 and the chassis 34 can thus be prevented even if the electronic cassette 30 is imparted with a vibration and the bend portion of the flexible substrate 20 deforms by the maximum dimension D3 towards the side of the end portion of the chassis 34 (in the depth direction of the base concave portion 36), due to provision of the base concave portion 36.

As a result noise due to the flexible substrate 20 contacting the chassis 34 can be prevented from occurring.

Other portions of the configuration are similar to those of the first exemplary embodiment and so further explanation thereof is omitted.

Third Exemplary Embodiment

Figure 4A:
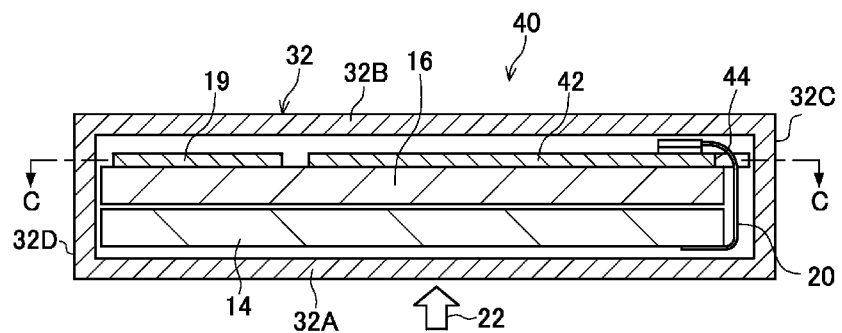
FIG. 4A is a vertical cross-section illustrating a basic configuration of a portable radiographic imaging device according to a third exemplary embodiment of the present invention.
Figure 4B:
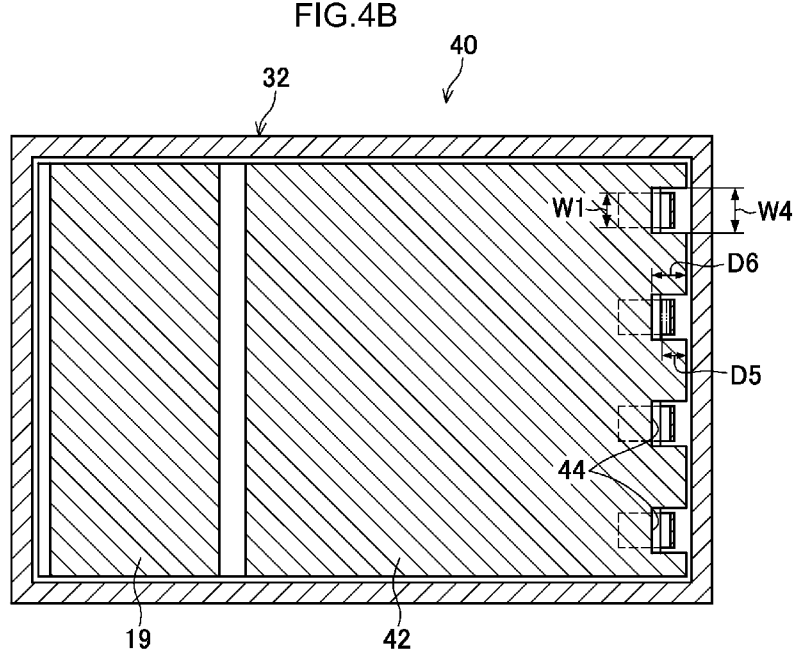
FIG. 4B is a cross-section taken along line C-C of FIG. 4A.

As shown in the cross-sections of FIG. 4A and FIG. 4B, an electronic cassette 40 of a third exemplary embodiment differs from the first exemplary embodiment by way of the contact avoidance portion provided at the periphery of the flexible substrate 20. Explanation focusses on the differences to the first exemplary embodiment.

In the present exemplary embodiment, an end portion of an electronic substrate 42 installed in the casing 32 is formed to approach the vicinity of the inner wall of the casing 12, so, unless countermeasures are adopted, the flexible substrate 20 would make contact with the end portion of the electronic substrate 42 when the bend portion of the flexible substrate 20 is deformed. Contact avoidance portions (substrate concave portions) 44 are therefore provided at the end portion of the electronic substrate 42 to avoid such contact.

The substrate concave portion 44 is provided to the end portion of the electronic substrate 42 at a position facing to the flexible substrate 20, and with a width W4 that is wider than the width W1 of the flexible substrate 20.

A depth D6 of the substrate concave portion 44 is set at a depth such that the flexible substrate 20 does not make contact with the electronic substrate 42 even if the electronic cassette 40 is imparted with a vibration and the bend portion of the flexible substrate 20 deforms towards an end portion of (in the depth direction) of the substrate concave portion 44 by a maximum dimension D5 (D6>D5).

Due to this configuration, contact between the flexible substrate 20 and the electronic substrate 42 can thus be prevented even if the electronic cassette 40 is imparted with a vibration and the bend portion of the flexible substrate 20 deforms by the maximum dimension D5 towards the side of the end portion of the electronic substrate 42.

As a result noise due to the flexible substrate 20 contacting the electronic substrate 42 can be prevented from occurring.

Other portions of the configuration are similar to those of the first exemplary embodiment and so further explanation thereof is omitted.

Fourth Exemplary Embodiment

Figure 5A:
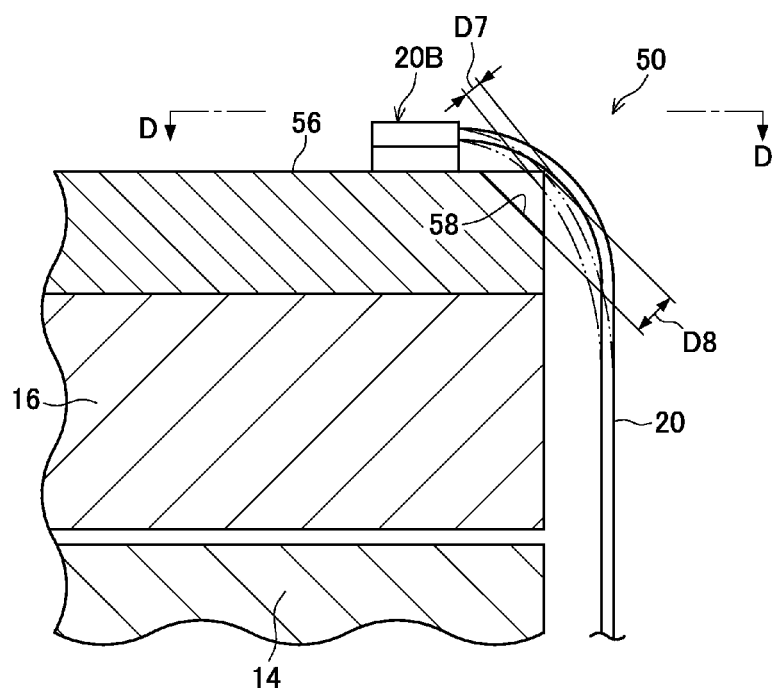
FIG. 5A is a partial cross-section illustrating a basic configuration of a portable radiographic imaging device according to a fourth exemplary embodiment of the present invention.
Figure 5B:
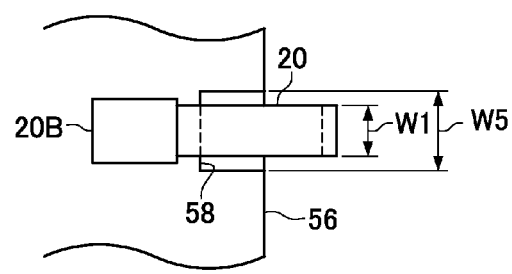
FIG. 5B is a drawing viewed from line D-D of FIG. 5A.

As shown in the cross-sections of FIG. 5A and FIG. 5B, an electronic cassette 50 of the fourth exemplary embodiment differs from the first exemplary embodiment by way of the contact avoidance portion provided at the periphery of a flexible substrate 20. Explanation follows focusing on the differences to the first exemplary embodiment.

In the present exemplary embodiment, an electronic substrate 56 installed in the casing 12 is formed to approach the vicinity of the inner wall of the casing 12. A corner portion of the electronic substrate 56 would therefore make contact with the flexible substrate 20 when the bend portion of the flexible substrate 20 deforms, unless countermeasures are adopted. Chamfered portions 58 are accordingly provided to the corner portion of the electronic substrate 56 as contact avoidance portions.

The chamfered portion 58 is provided to the corner portion of the electronic substrate 42 at a position facing to the flexible substrate 20 with a width W5 that is wider than a width W1 of the flexible substrate 20. The cutaway depth D8 of the chamfered portion 58 is set at a depth such that the flexible substrate 20 and the electronic substrate 42 do not make contact even if the bend portion of the flexible substrate 20 has deformed towards the end portion of the chamfered portion 58 by a maximum dimension D7 (D8>D7). The cutaway (chamfered) depth of the electronic substrate 56 can accordingly be made smaller than the depth of the substrate concave portion 44 of the third exemplary embodiment.

Due to this configuration, contact between the flexible substrate 20 and the electronic substrate 56 can thus be prevented even if the electronic cassette 50 is imparted with a vibration and the bend portion of the flexible substrate 20 deforms by the maximum dimension D7 towards the side of the end portion of the electronic substrate 56. As a result noise generated by the flexible substrate 20 can be suppressed.

Other portions of the configuration are similar to those of the first exemplary embodiment and so further explanation thereof is omitted.

Fifth Exemplary Embodiment

Figure 6A:
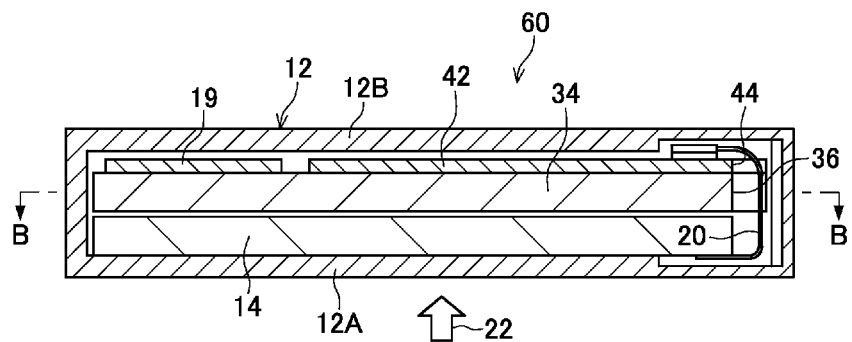
FIG. 6A is a vertical cross-section illustrating a basic configuration of a portable radiographic imaging device according to a fifth exemplary embodiment of the present invention.
Figure 6B:
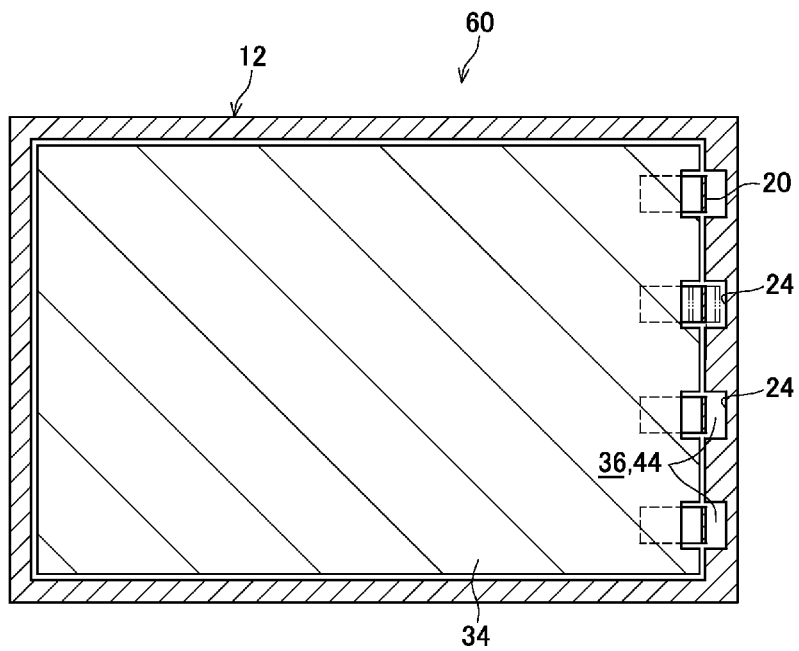
FIG. 6B is a cross-section taken along line B-B of FIG. 6A.

As shown in the cross-sections of FIG. 6A and FIG. 6B, an electronic cassette 60 according to the fifth exemplary embodiment differs from the first exemplary embodiment by way of the contact avoidance portions provided at the periphery of a flexible substrate 20. Explanation follows focusing on the differences to the first exemplary embodiment.

The present exemplary embodiment is configured by using all three types of contact avoidance portions explained in the first exemplary embodiment, the second exemplary embodiment and the third exemplary embodiment.

More specifically, the casing concave portions 24 explained in the first exemplary embodiment are provided to the inner wall of the casing 12 of the electronic cassette 60, the substrate concave portions 44 explained in the third exemplary embodiment are provided to the end portion of the electronic substrate 42, and the base concave portions 36 explained in the second exemplary embodiment are provided to the end portion of the chassis 34.

Due to this configuration, contact between the flexible substrate 20 and the inner wall of the casing 12, contact between the flexible substrate 20 and the chassis 34, contact between the flexible substrate 20 and the electronic substrate 42 can thus be prevented even if the electronic cassette 60 is imparted with a vibration and the bend portion of the flexible substrate 20 deforms by the maximum dimension D3 towards the inner wall of the casing 12, the side of the end portion of the chassis 34 and the side of the end portion of the electronic substrate 42, due to provision of the respective contact avoidance portions.

As a result noise generation arising from contact between the flexible substrate 20 and peripheral components thereto can be suppressed.

While omitted in the drawings, configuration may be made, for example, such that in a case in which the contact position between the flexible substrate 20 and the electronic substrate 42 is limited to a part of the end face of the electronic substrate 42, the chamfered portion 58 explained in the fourth exemplary embodiment is used in place of the substrate concave portion 44 explained in the third exemplary embodiment. Such an approach enables noise generation at the flexible substrate 20 to be suppressed by using only a small cutaway amount.

Other portions of the configuration are similar to those of the first exemplary embodiment and further explanation thereof is omitted.

Sixth Exemplary Embodiment

As shown in the cross-sections of FIG. 7A and FIG. 7B, an electronic cassette 64 according to a sixth exemplary embodiment differs from the first exemplary embodiment by way of the contact avoidance portions provided at the periphery of a flexible substrate 20. Explanation follows focusing on the differences to the first exemplary embodiment.

In the present exemplary embodiment configuration is made using the two types of contact avoidance portion explained in the first exemplary embodiment and the second exemplary embodiment.

More specifically, the casing concave portions 24 explained in the first exemplary embodiment are provided to the inner wall of the casing 12 of the electronic cassette 64, and the base concave portions 36 explained in the second exemplary embodiment are provided to the end portion of the chassis 34.

Due to this configuration, contact between the flexible substrate 20 and the chassis 34 can thus be prevented even if the electronic cassette 64 is imparted with a vibration and the bend portion of the flexible substrate 20 deforms by the maximum dimension D3 towards the side of the inner wall of the casing 12, the side of the end portion of the chassis 34 and the end portion of the electronic substrate 42.

As a result noise generation arising from contact between the flexible substrate 20 and peripheral components thereto can be suppressed. Other portions of the configuration are similar to those of the first exemplary embodiment and so further explanation thereof is omitted.

Note that, due to the base concave portions 36 being formed in the chassis 34 at positions facing to the casing concave portions 24, so sharing the contact avoidance function with the base concave portions 36 and the casing concave portions 24, the depth of the casing concave portions 24 may be formed shallower than in a case in which the base concave portions 36 are not formed to the chassis 34 (for example in the first exemplary embodiment). Any reduction in strength of the casing 12 can accordingly be suppressed.

Seventh Exemplary Embodiment

Figure 8A:
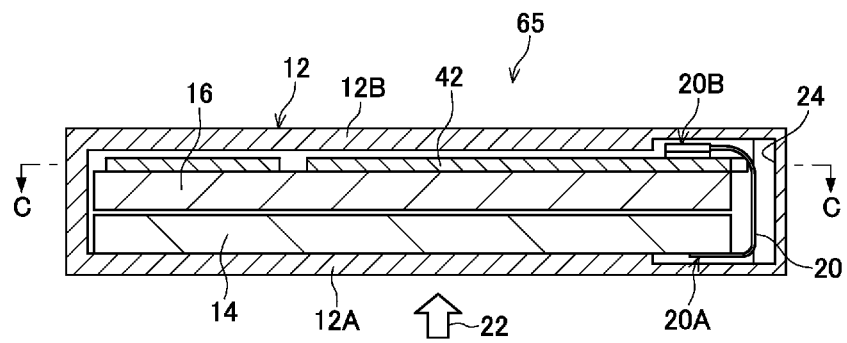
FIG. 8A is a vertical cross-section illustrating a basic configuration of a portable radiographic imaging device according to a seventh exemplary embodiment of the present invention.
Figure 8B:
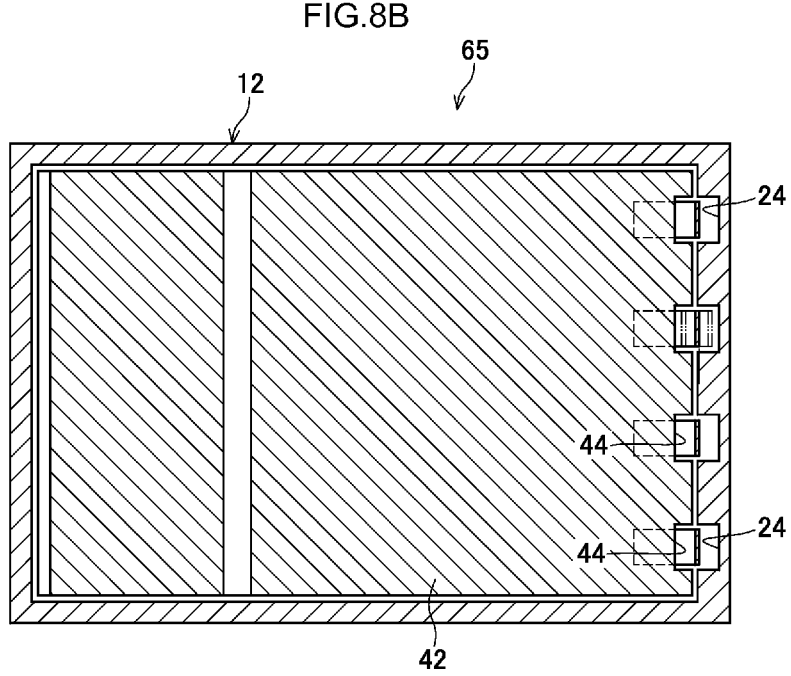
FIG. 8B is a cross-section taken along line B-B of FIG. 8A.

As shown in the cross-sections of FIG. 8A and FIG. 8B, an electronic cassette 65 according to the seventh exemplary embodiment differs from the first exemplary embodiment by way of the contact avoidance portions provided at the periphery of a flexible substrate 20. Explanation follows focusing on the differences to the first exemplary embodiment.

The present exemplary embodiment is configured by using the two types of contact avoidance portions explained in the first exemplary embodiment and the third exemplary embodiment.

Specifically, the casing concave portions 24 explained in the first exemplary embodiment are provided to the inner wall of the casing 12 of the electronic cassette 65, and the substrate concave portions 44 explained in the third exemplary embodiment are provided to the end portion of the electronic substrate 42.

Due to this configuration, contact between the flexible substrate 20 and the inner wall of the casing 12, contact between the flexible substrate 20 and the end portion of the chassis 16 and contact between the flexible substrate 20 and the end portion of the electronic substrate 42 can be prevented even if the electronic cassette 65 is imparted with a vibration and the bend portion of the flexible substrate 20 deforms by the maximum dimension D3 towards the inner wall of the casing 12, the side of the end portion of the chassis 16 and the side of the end portion of the electronic substrate 42.

As a result noise due to contact between the flexible substrate 20 and peripheral components thereto can be suppressed from occurring.

Note that, due to the substrate concave portions 44 being formed to the electronic substrate 42 at positions facing to the casing concave portions 24, so sharing the contact avoidance function with the substrate concave portions 44 and the casing concave portions 24, the depth of the casing concave portions 24 can be formed shallower than in a case in which the substrate concave portions 44 are not formed to the electronic substrate 42 (for example in the first exemplary embodiment). Any reduction in strength of the casing 12 can accordingly be suppressed.

While not shown in the drawings, configuration may be made, for example, such that in a case in which the contact position between the flexible substrate 20 and the electronic substrate 42 is limited to a part of the end face of the electronic substrate 42, the chamfered portion 58 explained in the fourth exemplary embodiment is used in place of the substrate concave portions 44 explained in the third exemplary embodiment. Such an approach enables noise generation at the flexible substrate 20 to be suppressed.

Other portions of the configuration are similar to those of the first exemplary embodiment and further explanation thereof is omitted.

Eighth Exemplary Embodiment

As shown in the cross-sections of FIG. 9A and FIG. 9B, an electronic cassette 66 according to the eighth exemplary embodiment differs from the first exemplary embodiment by way of the contact avoidance portions provided at the periphery of the flexible substrate 20. Explanation follows focusing on the differences to the first exemplary embodiment.

The present exemplary embodiment is configured by using the two types of contact avoidance portions explained in the second exemplary embodiment and the third exemplary embodiment.

Specifically, in the vicinity of the inner wall of the casing 32 in the electronic cassette 66, the substrate concave portions 44 explained in the third exemplary embodiment are provided to the electronic substrate 42, and the base concave portions 36 described in the second exemplary embodiment are provided to the end portion of the chassis 34.

Due to this configuration, contact between the flexible substrate 20 and the inner wall of the casing 32, contact between the flexible substrate 20 and the end portion of the chassis 34 and contact between the flexible substrate 20 and the end portion of the electronic substrate 42 can be prevented even if the electronic cassette 66 is imparted with a vibration and the bend portion of the flexible substrate 20 is displaced (deformed) by the maximum dimension D3 towards the inner wall of the casing 32, the side of the end portion of the chassis 34 and the side of the end portion of the electronic substrate 42.

As a result noise at the flexible substrate 20 is suppressed from occurring.

While not shown in the drawings, configuration may be made, for example, such that in a case in which the contact position between the flexible substrate 20 and the electronic substrate 42 is limited to a part of the end face of the electronic substrate 42, the chamfered portion 58 explained in the fourth exemplary embodiment is used in place of the substrate concave portion 44 explained in the third exemplary embodiment. Such an approach enables noise generation at the flexible substrate 20 to be suppressed.

Other portions of the configuration are similar to those of the first exemplary embodiment and further explanation thereof is omitted.

Ninth Exemplary Embodiment

Figure 10A:
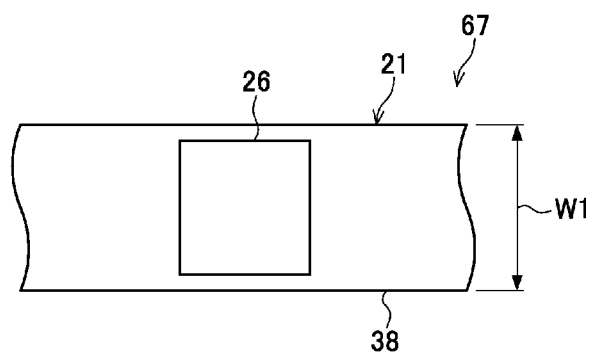
FIG. 10A is a face-on view illustrating a basic configuration of a portable radiographic imaging device according to a ninth exemplary embodiment of the present invention, and is a partial exploded drawing viewed from direction B in FIG. 1A.

As shown in the partial expanded diagram of FIG. 10A, an electronic cassette 67 according to a ninth exemplary embodiment is configured using a flexible substrate 21 in place of the flexible substrate 20 explained in the first exemplary embodiment. Explanation focusses on the difference to the first exemplary embodiment.

The flexible substrate 21 according to the present exemplary embodiment is configured with an amplifier 26 mounted partway a conductive cable portion 38 of the flexible substrate 21. The amplifier 26 has capability to amplify input electrical signals and output the input electrical signals, and is, for example, a charge amplifier.

In such a configuration, by the mounted amplifier 26, input electrical signals can be amplified and output in the flexible substrate 21. The electronic cassette 67 is thereby made more compact.

Note that the flexible substrate 21 of the present exemplary embodiment may be applied not only to the first exemplary embodiment, but also to the electronic cassettes of any of the second exemplary embodiment to the eighth exemplary embodiment.

Tenth Exemplary Embodiment

Figure 10B:
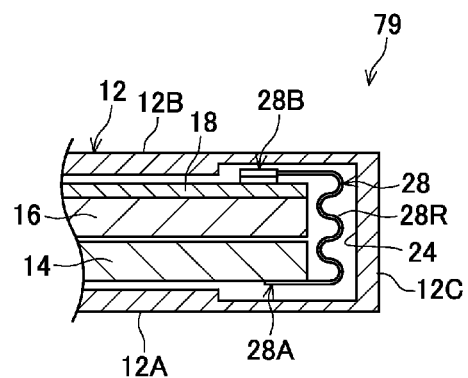
FIG. 10B is a partial cross-section illustrating a basic configuration of a portable radiographic imaging device according to a tenth exemplary embodiment of the present invention.

As shown in the cross-section of FIG. 10B, an electronic cassette 79 according to a tenth exemplary embodiment is configured using a flexible substrate 28 in place of the flexible substrate 20 explained in the first exemplary embodiment. Explanation focusses on the differences to the first exemplary embodiment.

One end of the flexible substrate 28 according to the present exemplary embodiment is connected to the flat panel sensor section 14 with the connection section 28A, and the other end is connected to the electronic substrate 18 with the connection section 28B. A portion of the flexible substrate 28 other than the connection sections is formed with a folded section 28R in which plural foldings are performed (provided) in the flexible substrate 28.

In the present exemplary embodiment, the folded section 28R is capable of deformation under external force, and acts flexed deformable portion of the flexible substrate 28.

By making such a configuration, the profile of the bend portion of the flexible substrate 28 can be made to a straight-line like shape, and contact avoidance portions formed to components peripheral to the flexible substrate 28 can be made shallower (smaller-depth). As a result, any reduction in strength of the peripheral components is suppressed, and contact between the flexible substrate 28 and components peripheral thereto can be suppressed.

What is claimed is:

1. A portable radiographic imaging device comprising:
   a radiation detection panel that includes optoelectric conversion elements that convert irradiated radiation into an electrical signal;
   a signal processing substrate that performs predetermined signal processing on the input electrical signal;
   a holding base that is provided between the radiation detection panel and the signal processing substrate and that holds the signal processing substrate;
   a flexible substrate that includes a flexed portion, with one end of the flexible substrate being connected to the radiation detection panel and the other end of the flexible substrate being connected to the signal processing substrate;
   a casing in which the radiation detection panel, the signal processing substrate, the holding base and the flexible substrate are installed; and
   a contact avoidance portion that is formed at at least one of the signal processing substrate, the holding base or the casing such that contact of the at least one of the signal processing substrate, the holding base or the casing with the flexible substrate is avoided.

2. The portable radiographic imaging device of claim 1, wherein the contact avoidance portion is a casing concave portion that is provided at an inner wall of the casing at a position facing the flexible substrate, and a width of the casing concave portion is wider than a width of the flexible substrate.

3. The portable radiographic imaging device of claim 2 further comprising a rib portion that maintains strength of the casing, the rib portion being formed between adjacent casing concave portions.

4. The portable radiographic imaging device of claim 1, wherein the contact avoidance portion is a base concave portion that is provided at an end portion of the holding base at a position facing the flexible substrate, and a width of the base concave portion is wider than the width of the flexible substrate.

5. The portable radiographic imaging device of claim 1, wherein the contact avoidance portion is a substrate concave portion that is provided at an end portion of the signal processing substrate at a position facing the flexible substrate, and a width of the substrate concave portion is wider than the width of the flexible substrate.

6. The portable radiographic imaging device of claim 1, wherein the contact avoidance portion is a chamfered portion that is provided at an end face of the signal processing substrate at a position facing the flexible substrate, and a width of the chamfered portion is wider than the width of the flexible substrate.

7. The portable radiographic imaging device of claim 1, wherein the contact avoidance portion includes:
   a casing concave portion that is provided at an inner wall of the casing at a position facing the flexible substrate, and a width of the casing concave portion is wider than a width of the flexible substrate,
   a base concave portion that is provided at an end portion of the holding base at a position facing the flexible substrate, and a width of the base concave portion is wider than the width of the flexible substrate, and
   a substrate concave portion that is provided at an end portion of the signal processing substrate at a position facing the flexible substrate, and a width of the substrate concave portion is wider than the width of the flexible substrate.

8. The portable radiographic imaging device of claim 1, wherein the contact avoidance portion includes:
   a casing concave portion that is provided at an inner wall of the casing at a position facing the flexible substrate, and a width of the casing concave portion is wider than a width of the flexible substrate, and
   a base concave portion that is provided at an end portion of the holding base at a position facing the flexible substrate, and a width of the base concave portion is wider than the width of the flexible substrate.

9. The portable radiographic imaging device of claim 8, wherein a depth of the casing concave portion in a case in which the base concave portion is formed at the holding base facing the casing concave portion is set shallower than a depth of the casing concave portion in a case in which the base concave portion is not formed at the holding base facing the casing concave portion.

10. The portable radiographic imaging device of claim 1, wherein the contact avoidance portion includes:
   a casing concave portion that is provided at an inner wall of the casing at a position facing the flexible substrate, and a width of the casing concave portion is wider than a width of the flexible substrate, and
   a substrate concave portion that is provided at an end portion of the signal processing substrate at a position facing the flexible substrate, and a width of the substrate concave portion is wider than the width of the flexible substrate.

11. The portable radiographic imaging device of claim 10, wherein a depth of the casing concave portion in a case in which the substrate concave portion is formed at the signal processing substrate facing the casing concave portion is set shallower than a depth of the casing concave portion in a case in which the substrate concave portion is not formed at the signal processing substrate facing the casing concave portion.

12. The portable radiographic imaging device of claim 1, wherein the contact avoidance portion includes:
   a base concave portion that is provided at an end portion of the holding base at a position facing the flexible substrate, and a width of the base concave portion is wider than the width of the flexible substrate, and
   a substrate concave portion that is provided at an end portion of the signal processing substrate at a position facing the flexible substrate, and a width of the substrate concave portion is wider than the width of the flexible substrate.

13. The portable radiographic imaging device of claim 1, wherein an amplify section that amplifies the input electrical signal is provided at the flexible substrate.

14. The portable radiographic imaging device of claim 1, wherein the flexed portion of the flexible substrate is a bent portion that is bent to be away from end portions of the radiation detection panel, the signal processing substrate and the holding base.

15. The portable radiographic imaging device of claim 1, wherein the flexed portion of the flexible substrate is a folded portion including a plurality of foldings in the flexible substrate.

16. A radiographic imaging system comprising:
   a portable radiographic imaging device including:
      a radiation detection panel that includes optoelectric conversion elements that convert irradiated radiation into an electrical signal;
      a signal processing substrate that performs predetermined signal processing on the input electrical signal;
      a holding base that is provided between the radiation detection panel and the signal processing substrate and that holds the signal processing substrate;
      a flexible substrate that includes a flexed portion, with one end of the flexible substrate being connected to the radiation detection panel and the other end of the flexible substrate being connected to the signal processing substrate;
      a casing in which the radiation detection panel, the signal processing substrate, the holding base and the flexible substrate are installed; and
      a contact avoidance portion that is formed at at least one of the signal processing substrate, the holding base or the casing such that contact of the at least one of the signal processing substrate, the holding base or the casing with the flexible substrate is avoided.
   a radiation generating device that generates radiation; and
   an imaging controller that controls the portable radiographic imaging device and the radiation generating device,
   wherein, under control of the imaging controller, radiation is generated by the radiation generating device and the portable radiographic imaging device images the radiation that passes through a subject.

* * * * *